United States Patent [19]

Teather et al.

[11] Patent Number: 4,704,607
[45] Date of Patent: Nov. 3, 1987

[54] SYSTEM FOR REMOTELY ADJUSTING A PARAMETER OF AN ELECTRICAL CIRCUIT WITHIN AN ENCLOSURE

[75] Inventors: Roy Teather, Poole; Michael Scott, Dorset, both of England

[73] Assignee: Sieger Limited, England

[21] Appl. No.: 790,033

[22] Filed: Oct. 22, 1985

[30] Foreign Application Priority Data

Oct. 25, 1984 [GB] United Kingdom ............... 8426964

[51] Int. Cl.[4] ............ G05B 23/02; G08C 19/00
[52] U.S. Cl. ............... 340/825.07; 340/825.69; 340/825.72; 340/632; 73/1 G
[58] Field of Search ......... 340/825.07, 310 A, 825.06, 340/825.52, 825.54, 825.69, 825.72; 299/1; 73/1 G; 324/63

[56] References Cited

U.S. PATENT DOCUMENTS

| | | | |
|---|---|---|---|
| 3,559,177 | 1/1971 | Benson | 340/825.07 |
| 4,173,754 | 11/1979 | Feiker | 340/825.52 |
| 4,192,551 | 3/1980 | Weimer et al. | 299/1 |
| 4,386,436 | 5/1983 | Kocher et al. | 340/310 A |
| 4,418,333 | 11/1983 | Schwartzbach et al. | 340/825.07 |
| 4,476,706 | 10/1984 | Hadden et al. | 72/1 G |
| 4,494,399 | 1/1985 | Youngman | 73/1 G |

FOREIGN PATENT DOCUMENTS 57-97791 6/1982 Japan .............. 340/825.72

Primary Examiner—John W. Caldwell, Sr.
Assistant Examiner—Ralph E. Smith
Attorney, Agent, or Firm—Wolf, Greenfield & Sacks

[57] ABSTRACT

Gas sensors 1 are mounted on respective explosion proof housings 2 that contain microprocessor circuitry 11 for operating signals from the sensors. Signals from the circuitry 11 are transmitted along a digital highway 4 to a central control unit. The sensors may be located at remote locations in an industrial process plant or for example along the roof of a tunnel. A non-contact hand held unit 12 is provided for individually setting operating parameters of the circuitry 11, to enable factors such as zero set, span and linearity to be set for the sensors individually. A two way wireless communication link is provided between the unit 12 and a transducer 15 on the housing 1, so that the current value of the circuit operating parameters can be displayed on a display 18 on the hand held unit.

9 Claims, 4 Drawing Figures

# SYSTEM FOR REMOTELY ADJUSTING A PARAMETER OF AN ELECTRICAL CIRCUIT WITHIN AN ENCLOSURE

FIELD OF THE INVENTION

This invention relates to a system for permitting remote adjustment of a parameter of an electrical circuit within an enclosure exteriorly of the enclosure without changing the physical configuration of the enclosure.

The invention has particular but not exclusive application to adjusting a parameter of an electrical circuit used in a potentially explosive atmosphere.

BACKGROUND TO THE INVENTION

Conventionally, an electrical circuit in a potentially explosive atmosphere is housed in a enclosure comprising an explosion protected container which has a removable lid. The container and its lid usually comprise machined metal castings provided with cooperating internal lips and surfaces which prevent a flame front established by arcing from the circuit, propagating between the container and lid to establish an explosive condition exteriorly of the enclosure. The enclosure thus in practice cannot be opened in an explosive atmosphere to allow adjustment of the circuit, since a risk of explosion would then occur. It is accordingly difficult to adjust the circuit whilst in use in a potentially explosive atmosphere. It has been proposed to provide an explosion protected enclosure with a potentiometer inside the enclosure, the potentiometer having an adjustment screw on the outside of the enclosure. Whilst this arrangement does permit circuit adjustments to be made, the enclosure is of a complex construction and only a limited adjustment can be made. Also, it is not readily possible to monitor the adjustment that actually has been made, nor is it possible to make the adjustment from a remote location.

SUMMARY OF THE INVENTION

Broadly stated, the present invention provides a system for permitting remote adjustment of a parameter of an electrical circuit within an enclosure comprising: an enclosure; an electrical circuit within the enclosure, said circuit having an adjustable value circuit parameter; control means remote from the enclosure, for transmitting command signals for adjusting said parameter and for receiving current value signals representative of the value of said circuit parameter; and transducer means associated with the circuit and the enclosure, the transducer means being operative to transmit said current value signals to the remote control means, and said transducer means being responsive to said command signals such as to adjust the value of said circuit parameter.

In accordance with a preferred example of the invention for an explosion protected enclosure, the transducer means comprises a transmitter and receiver for radiation such as infra-red, ultrasonic or r.f. radiation, mounted in or on the enclosure, typically on the exterior thereof, such that the enclosure is closed in a flame-proof manner, with the transducer electrically connected to circuits within the enclosure. The remote control unit may comprise a hand held unit with a corresponding radiation transmitter and receiver for communication with the transducer in or on the enclosure.

The invention can be used with advantage in a gas sensor system for a potentially explosive atmosphere.

The invention can also be used in non-potentially explosive atmospheres for adjusting circuits which are not readily physically accessible.

BRIEF DESCRIPTION OF THE DRAWINGS

In order that the invention may be more fully understood embodiments thereof will now be described by way of example with reference to the accompanying drawings wherein.

DESCRIPTION OF PREFERRED EMBODIMENT

Figure 1:
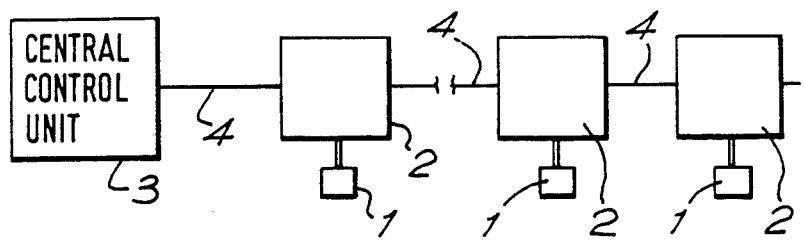
FIG. 1 is a schematic diagram of a gas sensor arrangement for use in a potentially explosive atmosphere.

Referring firstly to FIG. 1 there is shown an arrangement of gas sensors 1 which are each connected to respective control circuitry within an explosion protected enclosure 2. The sensors 1 may be located at different positions in an industrial process plant for monitoring the occurence of potentially hazardous atmospheric conditions, for example a potentially explosive atmosphere. Alternatively, the sensors may be disposed linearly along the length of a tunnel for monitoring atmospheric conditions.

The outputs of the sensors 1 are processed by the circuitry in the containers 2 and signals are applied to a central control unit 3 via a digital highway 4. The highway 4 comprises a digital data bus which permits data from the sensors 1 after processing by the circuit in the enclosure 2, to be transmitted to the central control unit 3, and also for commands to be transmitted from the central control unit 3 to the circuit in enclosure 2 individually. Each sensor 1 together with its associated enclosure 2 has an individual address. Operating parameters for each sensor 1 can be adjusted by means of appropriate commands from the central control unit 3.

The sensor is conveniently housed in an explosion protected housing attached to the enclosure 2. This housing may comprise Model 910 sensor housing manufactured by Sieger Limited, Poole, Dorset, England. The gas sensor may be of any suitable form for the contemplated hazardous environment. The sensor is typically an analog device and the circuits within the enclosure 2 are arranged to digitise the sensor output.

Figure 2:
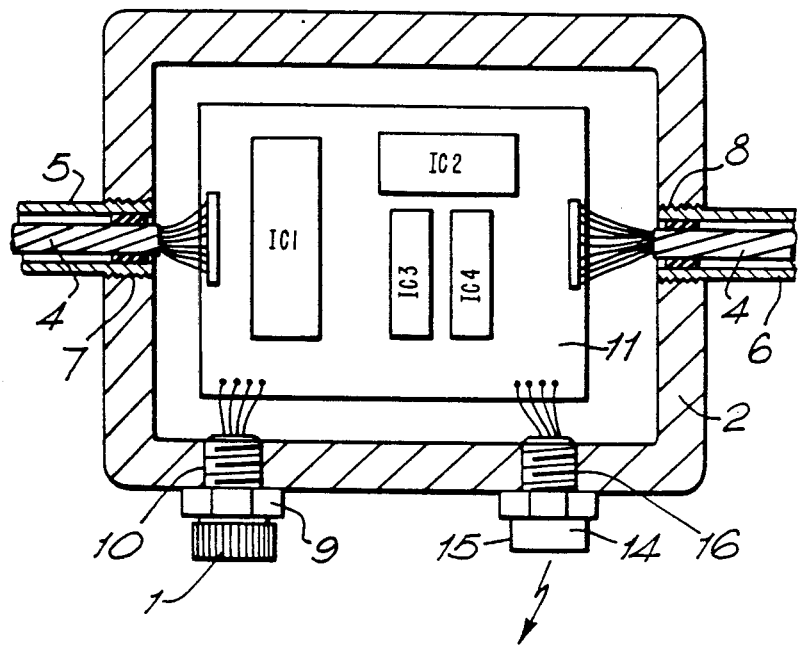
FIG. 2 illustrates in more detail one of the gas sensors of FIG. 1 and its associated circuitry, together with a hand held remote control unit for adjusting the circuitry.
Figure 2:
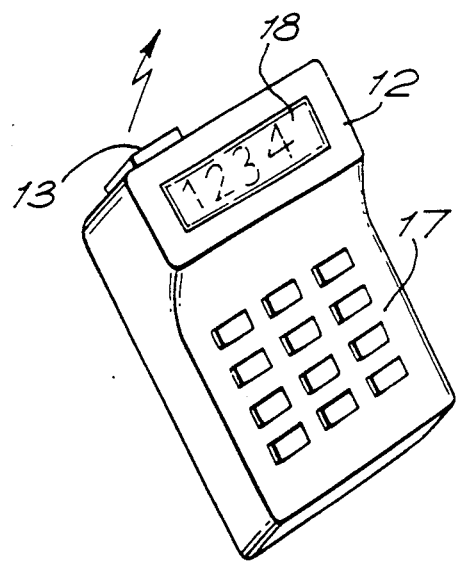

Referring now to FIG. 2, the arrangement of one of the sensors 1 and its associated enclosure 2 is shown in more detail. The enclosure 2 consists of a cast metal box provided with a metal lid (not shown). The enclosure and its lid are formed with a cooperating machined, flat surface to render the enclosure flame-proof when closed. The digital highway 4 consists of multicore cable received within conduits 5, 6 that have threaded ends received within threaded apertures 7, 8 in the enclosure 2. The gas sensor 1 is received within flame-proof housing 9 that is screwed into an aperture 10 in the enclosure 2.

The digital highway 4 and the sensor 1 are connected to control circuitry on a printed circuit board 11 within the enclosure 2. As is explained in more detail hereinafter circuitry IC1-IC4 on the board 11 is operative to digitise output signals from the sensor 1 and feed them to the digital highway 4 under the control of commands from the central control unit 3. The circuitry contains a microprocessor IC4 and permits operating parameters for the sensors to be reconfigured. Thus the following parameters may be altered; zero set, span, individual sensors address, linearisation curve, range, and alarm setting.

In practice, the central control unit may be several hundred metres away from the gas sensor, but it would be desirable to be able to set these parameters locally, i.e. in the vicinity of the sensor. However, in a potentially explosive atmosphere, the enclosure 2 cannot be opened with power applied because of the consequential risk of explosion. To overcome this problem, in accordance with the present invention, a hand held remote control unit 12 is provided.

The remote control unit 12 includes a battery driven transmit/receive unit 13 which communicates with a transducer 14 mounted in a gas tight housing 15 screwed into an aperture 16 in the enclosure 2. This transducer may also be incorporated behind a window in the enclosure wall. The remote control unit 12 includes a keyboard 17 which enables commands to be transmitted to the circuits within the enclosure 2 so as to change all or some or one of the previously mentioned operating parameters. Also, the transducer 14 is arranged to transmit back to the remote control unit 12 current values of the circuit parameters which are then displayed on a LCD or LED display 18 to enable the operator to determine the current values for circuit parameters.

Figure 3:
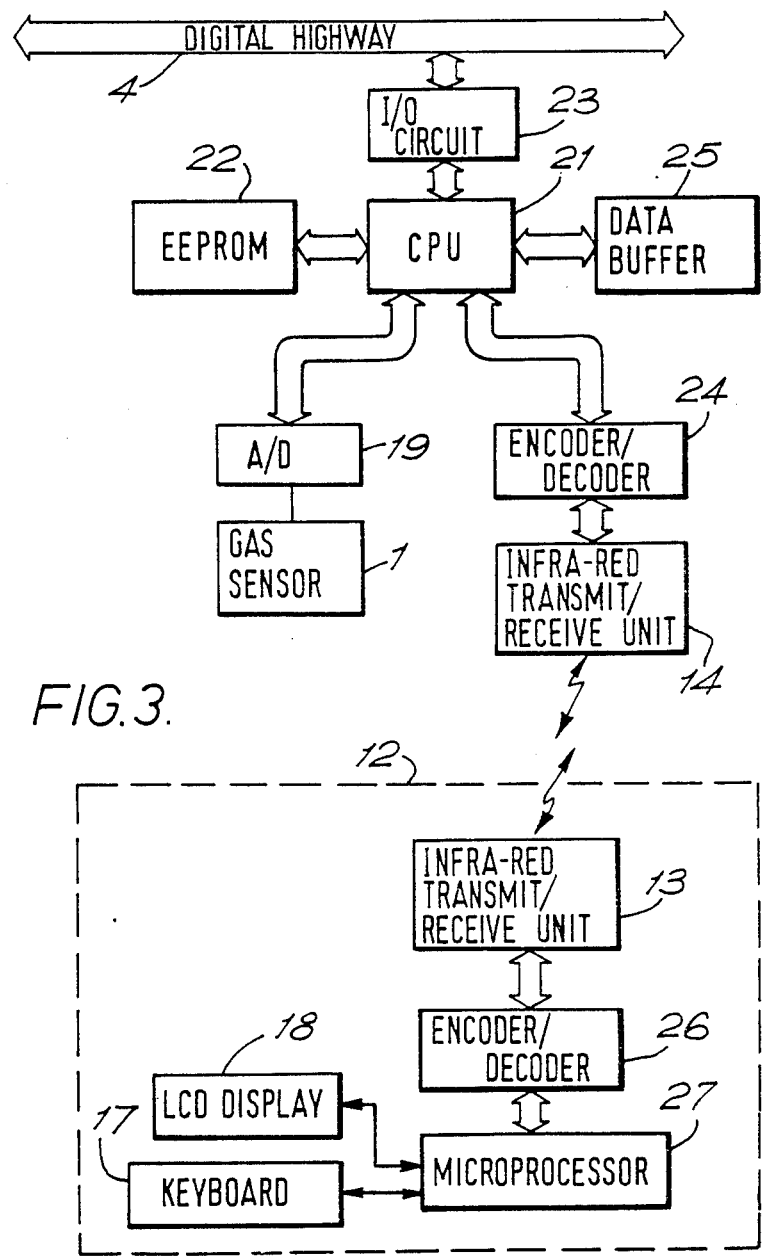
FIG. 3 is a schematic block diagram of the circuitry of the sensor and the remote control unit shown in FIG. 2.

The circuitry will now be described in more detail with reference to FIG. 3. Configuration information is held in the EEPROM 22 concerning zero setting offset, span offset, linearisation range etc. Analogue signals from the gas sensors 1 are fed to an analogue to digital converter circuit 19 which produces digital signals indicative of the gas sensor output. These digital signals are fed to the microprocessor CPU circuit 21. The digitised gas sensor signals are processed by the CPU 21 so as to modify the zero setting, span, linearisation, range etc. using the configuration information held in EEPROM 22. The processed signals are then held in a data buffer 25. Signals from the data buffer 25 are fed to the digital highway 4 under the control of an addressable input output circuit 23 which has a programmable address. Thus, in use, when the central controller 3 (FIG. 1) sends a particular address signal down the digital highway corresponding to the address for the circuit 23, data is fed from the data buffer 25 via the CPU to the digital highway and hence to the central controller 3. The processed signals are held in a buffer 25 and are available for the digital highway 4 via the addressable input output circuit 23 when the unit is addressed by the central controller 3.

The configuration information held in the EEPROM 22 is also available for the digital highway 4 via the addressable input output circuit 23 when the unit is addressed by the centrol controller 3 using special codes.

The CPU 21 is also connected to an encoder/decoder circuit 24 which supplies signals to and from the transducer 14. In this instance, the transducer 14 and corresponding transmit receive unit 13 operate in the infrared region. However, other radiatin could be used, for example ultrasound or rf radiation.

The transmit/receive unit 13 is connected to encoder/decoder 26 which in turn is connected to a microprocessor 27. The microprocessor 27 is connected to the keyboard 17 and the LCD display 18.

Thus, in use when an operator wishes to modify for example the zero-setting for the gas sensor 1, an appropriate command is keyed into the keyboard 17 and thereby transmitted by the unit 13 to the transducer 14 on the enclosure 2. Appropriate command signals are fed to the CPU 21 such that it processes the output of the analogue to digital converter 19 to provide the programmed zero setting offset for data stores in the EEPROM 22. The results of the change in zero setting are then fed back to the encoder/decoder 24 for transmission by the transducer 14 back to the hand held unit 12 for display on the LCD Display 18. Thus the operator can positively check the change in circuit parameter carried out by the keyed command.

The remote control unit has the advantage that the operator does not have to get into close proximity with the container 2, for example to adjust a potentiometer as in the prior art. Thus, the gas sensor could be mounted on a ceiling or a remote gantry but can still be adjusted by means of the remote control unit 12.

Figure 4:
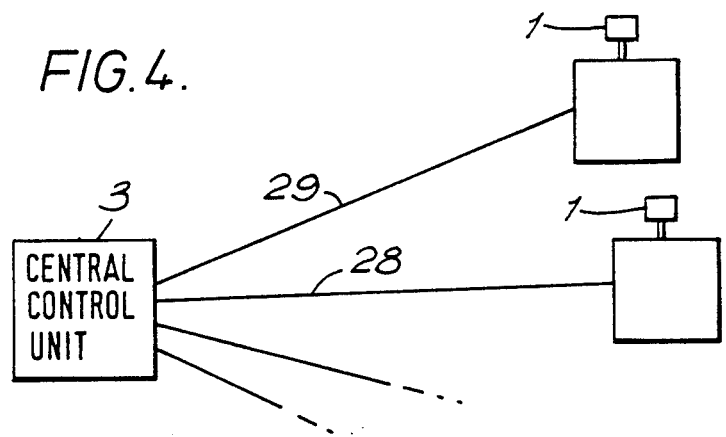
FIG. 4 is a schematic diagram of an alternative configuration of the gas sensors.

Many modifications to the described embodiment of the invention are possible. For example, the metal flameproof enclosure 2 could be replaced by an arrangement in which the circuit board 11 and ancillary circuits are completely encapuslated, since in accordance with the invention, there is no longer need to provide an openable enclosure for the circuit 11. Also, whilst in FIG. 1 the sensors 1 are shown serially connected to the data highway 4, other configurations are possible. For example, as shown in FIG. 4 the sensors 1 may be individually connected to the central control unit 3 by individual data lines 28, 29 etc. Also, whilst the data highway 4 in FIG. 1 is shown as a hard wired connection, the data highway could be provided by other means, for example optical fibres.

Furthermore, the invention has applications to arrangements other than gas sensing which need not necessarily be in potentially explosive atmospheres. For example, the invention has application to adjusting parameters of circuits which are not readily accessible. In certain apparatus, banks of circuitry may be provided which have parameters that need to be adjusted from time to time. The circuitry may not be physically readily accessible so that physical adjustment of potentiometers etc. may not be easily carried out. In accordance with the present invention, a transducer such as 14 may be provided on the circuitry and a hand held unit such as the unit 12 may be utilised to adjust the circuit parameters without the need actually to gain physical access to the circuit.

In addition it will be appreciated that the gas sensor 1 could be replaced by other sensors, for example fire sensors. Many other modifications and variations falling within the spirit and scope of the invention will be apparent to those skilled in the art.

What is claimed is:
1. In a sensor system comprising:
a central control unit at a first location;
a sensor station at a second location; and
a data link between the first and second locations;
said sensor station including sensor means, an explosion protected enclosure, an electric circuit within the enclosure and coupled to the sensor means to process signals therefrom and supply data to the central control unit via said data link, the circuit having a circuit parameter which is adjustable through a range of non-zero values, the improvement comprising means within the enclosure for producing a signal indicative of the current value of said adjustable circuit parameter;

portable control means remote from said enclosure, including means for transmitting command signals directly to the sensor station for adjusting the value of said circuit parameter, means for receiving directly from the sensor station current value signals representative of the current value of said circuit parameter, and means responsive to said received signals for displaying the current value of said circuit parameter;

transducer means at said sensor station and operative to transmit said current value signals from the enclosure to the portable control means and to receive said command signals from the remote control means; and means responsive to said received command signals for adjusting the value of said circuit parameter in accordance with said received command signals.

2. A sensor system according to claim 1 including a transmitted radiation link between said transducer means and said portable control means.

3. A system according to claim 1 wherein said sensor comprises a gas sensor.

4. A system according to claim 1 wherein said control means comprises a hand held unit operable remotely of said enclosure.

5. A system according to claim 4 wherein the hand held unit includes a keyboard for setting a desired value for the circut parameter.

6. A system according to claim 1 including a plurality of said enclosures and associated circuits, said circuits being connected to said central control unit.

7. A system according to claim 6 wherein the circuits are serially connected to the central control unit via a digital highway.

8. A system according to claim 6 wherein the circuits are selectively addressable by the central control unit.

9. A system according to claim 1 wherein said sensor produces an analog sensor signal, and said circuit includes digital conversion means for digitising said analog sensor signal, and microprocessor means responsive to said command signals to adjust at least one of a group of parameters comprising zero set, span, address, linearisation curve, range and alarm setting, for the sensor.

* * * * *